United States Patent [19]

Jones et al.

[11] Patent Number: 4,907,442
[45] Date of Patent: Mar. 13, 1990

[54] METHOD AND SYSTEM FOR DETERMINING FLUID SATURATIONS WITHIN NATURAL OR SIMULATED FRACTURES

[75] Inventors: Timothy A. Jones, Carrollton; Thomas J. Kaluza, Dallas, both of Tex.

[73] Assignee: Mobil Oil Corporation, New York, N.Y.

[21] Appl. No.: 325,593

[22] Filed: Mar. 20, 1989

[51] Int. Cl.$^4$ ............................ G01V 3/38; G01N 5/02
[52] U.S. Cl. ............................................ 73/38; 73/153; 324/376; 324/663; 324/698
[58] Field of Search ................. 73/38, 153; 324/376, 324/61 R, 61 P

[56] References Cited

U.S. PATENT DOCUMENTS

| | | | |
|---|---|---|---|
| 2,539,355 | 1/1951 | Reichertz | 73/38 |
| 2,745,057 | 5/1956 | Dotson . | |
| 2,781,488 | 2/1957 | Zimmerman et al. . | |
| 2,802,172 | 8/1957 | Mueller et al. . | |
| 2,802,173 | 8/1957 | Nible | 324/376 |
| 2,913,658 | 11/1959 | Burdine . | |
| 2,942,176 | 6/1960 | Brownscombe | 324/376 |
| 3,302,101 | 1/1967 | Glanville | 324/376 |
| 3,329,006 | 7/1967 | Silkin | 73/38 |
| 4,381,665 | 5/1983 | Levine | 73/153 |
| 4,482,634 | 11/1984 | Davis | 73/153 |
| 4,672,840 | 6/1987 | Cullick . | |
| 4,734,649 | 3/1988 | Barnaby | 324/376 |
| 4,786,873 | 11/1988 | Sherman | 324/376 |

Primary Examiner—Reinhard J. Eisenzopf
Assistant Examiner—Jose M. Solis
Attorney, Agent, or Firm—Alexander J. McKillop; Charles J. Speciale; Michael J. Mlotkowski

[57] ABSTRACT

A method and system for determining fluid saturation within a fracture. The method comprises the steps of establishing a functional relationship between fluid saturation and capacitance for a multiple component fluid; introducing the fluid between the fracture faces of the fractured media; measuring electrical capacitance between the fracture faces; and determining fluid saturation from the capacitance measurement and the functional relationship. The method and system find utility with both simulated and natural fractures.

21 Claims, 2 Drawing Sheets

METHOD AND SYSTEM FOR DETERMINING FLUID SATURATIONS WITHIN NATURAL OR SIMULATED FRACTURES

FIELD OF THE INVENTION

This invention relates to a method and system of measuring certain physical conditions of naturally fractured or simulated fractured media and, more particularly, to a method and system for determining fluid saturations within the fractures of such media.

BACKGROUND OF THE INVENTION

In the production of oil, gas and other minerals, certain properties of the subterranean reservoir must be determined. Two of the key, most commonly measured properties are the porosity and permeability of the reservoir. The porosity of a material is the ratio of the aggregate volume of its void or pore spaces (i.e., pore volume) to its gross bulk volume and, in the case of an oil or gas reservoir, is a measure of the capacity within the reservoir rock which is available for storing oil or gas. The permeability of a material is a measure of the ability of the material to transmit fluids through its pore spaces and is inversely proportional to the flow resistance offered by the material. Also, it is often desirable or necessary to measure other physical conditions of media material. Such conditions include, for example, the fluid saturation of the material. Fluid saturation affects the permeability of a reservoir. Thus, in the solution of many problems relating to the performance of a subterranean reservoir, it is necessary to measure the fluid saturation of a core sample taken from the reservoir. By saturation is meant the percentage of the pore volume filled with each of fluid phases contained within the sample. This measurement is required, among other reasons, for determination of the relative permeability of the media sample, i.e., the ratio of the permeability to a given fluid in the presence of another fluid or fluids and the permeability to the given fluid in the absence of any other fluid.

Porosity and permeability are determined by taking core samples from the reservoir site and carrying out well-defined measurement techniques on the samples. There are several techniques available for making such measurements, many of which are described in Petroleum Production Engineering Development by L. C. Uren, Fourth Edition, McGraw-Hill Book Company, Inc., 1956, pps 660-669. Another standard reference for core sample analysis is the API Recommended Practice of Core-Analysis Procedure, API RP40, American Petroleum Institute, 1960, 55 pps. While these procedures are suitable for measuring the porosity and permeability of a sample, they do not address techniques capable of adequately assessing the contribution of reservoir fractures to overall production.

Fluid saturations in reservoir cores and in formations are normally determined by electrical resistivity techniques. Resistivity techniques are described, generally, in Fundamentals of Formation Evaluation by D. P. Helander, OGCI Publications, Tulsa, OK, 1983, as well as in U.S. Pat. Nos. 2,745,057 and 2,802,172. These techniques develop a calibration curve for the matrix rock that is characteristic of the void spaces of the matrix. This is done by taking conductance measurements of the matrix at varying water saturation levels. This technique works well for cores with uniform pore spaces but does not work very well for vuggy cores or for cores with fractures. With regard to cores with fractures, the fractures act as a direct short for the measurement and yield results that are not representative of the total core. Because of this, analysis of fluid saturations in fractures cannot be determined by resistance techniques.

Fractures play an important role in reservoir behavior, having the ability to either enhance or restrict fluid flow in reservoirs. Furthermore, fractures can alter the apparent permeability and/or pososity of the rock. Because of these important influences, the impact of fractures on reservoir behavior must be fully understood in order to accurately model and effectively engineer a given reservoir.

All reservoirs are probably fractured to some extent. Reservoir fracture systems are often complicated, interconnected arrays of fluid flow paths. In fractured reservoirs the preferred flow path is established through these interconneting fractures since they exhibit higher permeability (lower resistance to flow) than does the porous matrix. However, like porous media, relative permeability curves are needed to accurately describe multi-phase flow in fractures. Before the interconnected array can be studied, the simplest case of a single fracture must be studied.

It is therefore an object of this invention to provide a method and system for determining the fluid saturation of a natural or simulated fracture.

It is another object of this invention to provide a method and system for determining the fluid saturation of a natural or simulated fracture present within a core sample.

It is a further object of this invention to provide a method and system for determining the water saturation of a natural or simulated fracture present within a core sample which contains at least one other fluid phase.

It is yet another object of this invention to provide a method and system for determining the fluid saturation of a natural or simulated fracture present within a core sample during measurement of relative permeability.

Other objects of the invention will become apparent from the following detailed description thereof.

SUMMARY OF THE INVENTION

According to the present invention, for a fractured material, there is provided a method for determining fluid saturation within a fracture having at least first and second fracture faces comprising the steps of establishing a functional relationship between fluid saturation and capacitance for a multiple component fluid, passing the fluid between the fracture faces, measuring capacitance between the fracture faces and determining fluid saturation from the capacitance measurement and the relationship so established. The method is useful under both static and dynamic conditions and under conditions of multi-phase flow. A system for carrying out the method of this invention is also provided.

BRIEF DESCRIPTION OF THE DRAWINGS

The actual construction, operation and advantages of the present invention will be better understood by referring to the following drawings in which like numerals identify like parts and in which.

DETAILED DESCRIPTION OF THE PREFERRED EMBODIMENT

Figure 1:
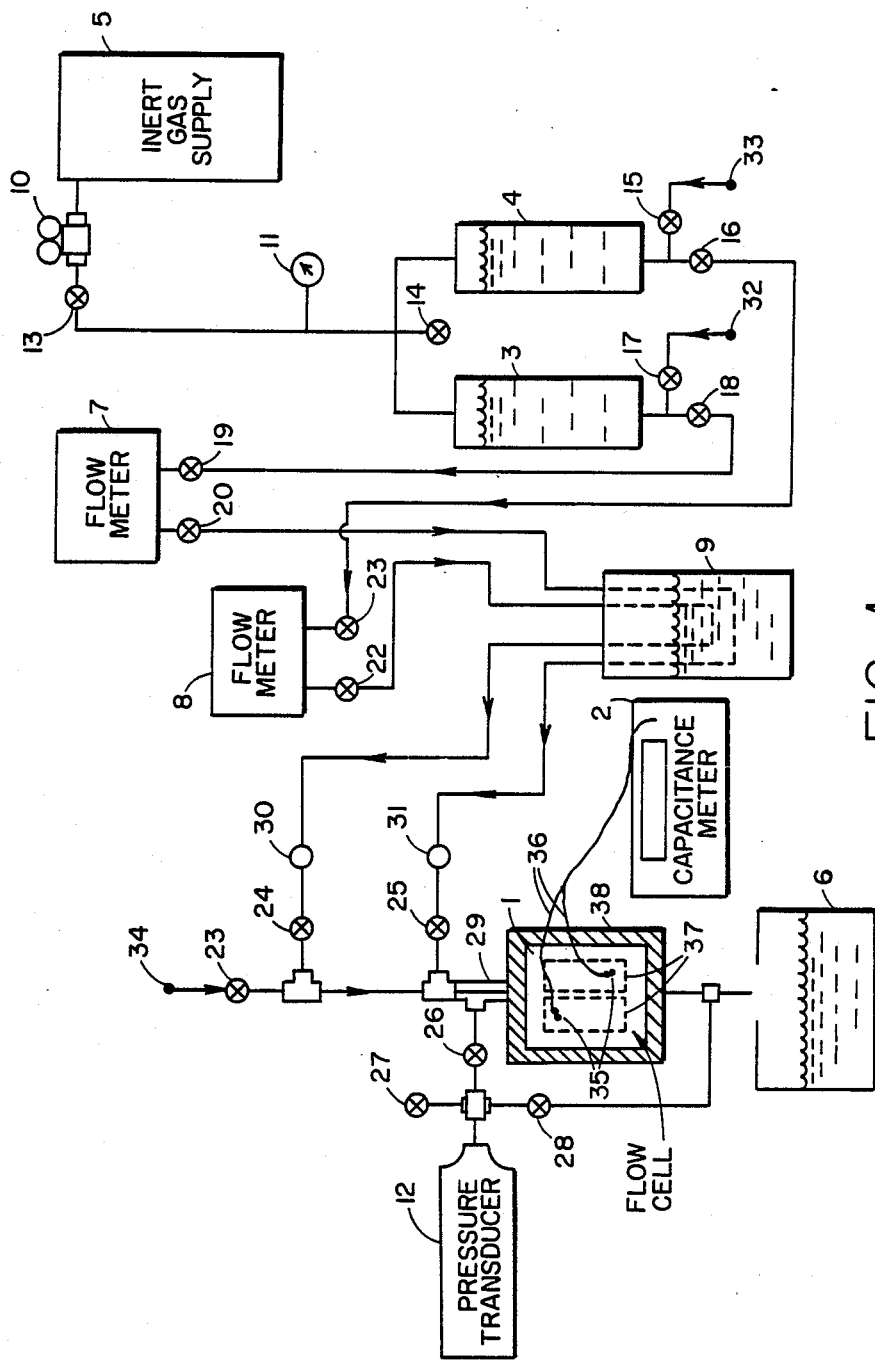
FIG. 1 is a schematic representation of the system for carrying out the fluid saturation determination of the method of the present invention.

Resistance techniques to determine fluid saturations will not work for fractures since the fracture creates an open electrical circuit. To analytically determine fluid saturations in fractures, the present invention provides a capacitance technique that will work for non-contacting conductive fracture surfaces.

Capacitance is a function of several parameters; surface area, plate separation, voltage and material between the plates. In the invention disclosed herein, the fracture surfaces, or faces, act as the capacitor plates. The separation of the plates is represented by the fracture aperture, and the material between the plates is the test fluid. For a particular test, these parameters are held constant except for the test fluid between the plates, which advantageously may be varied and comprise a multi-phase fluid.

In electrical theory, the material between a capacitor's parallel plates is called a dielectric. The dielectric material in a capacitor changes the capacitance of the capacitor by a factor related to the materials dielectric constant. As noted in University Physics by F. W. Sears et al., air has a dielectric constant of 1, water, a dielectric constant of 78 and decane, a dielectric constant of 2. Since the dielectric constant is a proportionality constant in the capacitance equation, a capacitor with water as the dielectric would have a capacitance 78 times higher than that of an identical capacitor with a dielectric of air.

If a capacitor has two dielectric materials between its plates, then the total capacitance of the capacitor should be related to the total volume of each material between its plates and the dielectric constant of each. This concept can be directly related to fluid saturations and volumes of fluids present within a fracture.

If the fluids between the plates of a capacitor have different dielectric constants, then this difference will enable mixtures of the two fluids to be calculable. For example, knowing the capacitance at 100% water saturation and at 100% decane saturation for a given fracture, intermediate fractional combinations of each can be calculated, providing the relationship of saturation versus capacitance between these two values is linear or at least known.

For example:
Assume for a given fracture:
$C_{H2O}(100\%) = 120\ \mu F$
$C_{C10}(100\%) = 3\ \mu F$ where $C_{H2O}(100\%)$ is the capacitance, in micro farads ($\mu F$) measured between the fracture faces when the volume between same is filled with water; and $C_{C10}(100\%)$ is the capacitance, in $\mu F$ measured between the fracture faces when the volume between same is filled with decane.

If a mixture of these fluids yields a capacitance reading, $C_{(n)}$ of 34 $\mu F$ then:

$100 \times (C_{(n)} - C_{C10}(100\%))/(C_{H2O}(100\%) - C_{C10}(100\%)) = S_{H2O(n)}$   Eq. 1

$100(34-3)/(120-3) = S_{H2O}(\%\ \text{water saturation})$ $S_{H2O} = 26.5\%$

Any material having a natural or simulated fracture is envisioned as being useful in the practice of the present invention, so long as the fracture faces are conductive. For example, to simulate an actual rock fracture for modeling purposes, a fracture may be formed from a pair of aluminum blocks, with the aperture of this simulated fracture set as desired. A more realistic fracture can be simulated by glueing sand grains to a pair of conductive metal surfaces so that the impact of surface roughness may be simultaneously studied.

Naturally fractured media is of particular interest to those skilled in the art of reservoir production modeling. However, core samples obtained from such oil-bearing rock are not naturally conductive and must be modified to be conductive to be useful in the practice of this invention. For capacitance measurements to be taken using naturally-fractured cores, the parallel fracture faces can be finely coated with a conductive material such as gold. A sputter coater is particularly useful and preferred for this operation. Sputter coating is a well-known technique as evidenced by U.S. Pat. Nos. 4,198,283, 4,743,570, 4,745,297, 4,756,815 and 4,767,678, incorporated by reference herein.

Generally, sputter coating requires the use of a sputtering source, an example of which may be found described in detail in U.S. Pat. No. 4,100,055, issued July 11, 1978 to R. M. Rainey for "Target Profile for Sputtering Apparatus". Such a sputtering source is also commercially available from and manufactured by Varian Associates, Inc. under the registered trademark "S-Gun". Such sputter coating sources employ a magnetically confined gas discharge and require a subatmospheric inert gas environment such as argon. Other sputtering sources with ring-shaped targets exist as, for example, a planar magnetron source. Positive ions from the gas discharge strike the target, which is made of the source material for the coating which is desired to be deposited, for example gold. Thus, source material is caused to be sputtered from the target outwardly from the source. The sputter coating process is carried out in a substmospheric controlled environment of a vacuum chamber, within which the dominant gas, which is normally argon, is deliberately introduced at very low pressures to sustain the gas discharge. The argon pressure required to sustain the discharge is generally in the range 2–20 microns.

The practice of this invention in conjunction with naturally fractured media samples is not limited to the use of a sputter coating process to provide the requisite conductive fracture faces and any means capable of providing same is envisioned as useful in the method and system disclosed herein.

Reference is now made to FIG. 1 which presents a detailed schematic of a system preferred for carrying out the method of this invention. As with all figures presented herein, FIG. 1 is given by way of example and illustration and not of limitation.

As may be comprehended from FIG. 1, the preferred system advantageously comprises a flow cell assembly 1, for mounting the fractured material 37 therein, a capacitance meter 2 for measuring the capacitance between the fracture faces when an electrical potential exists across same and a fluidic supply, control and monitoring system 3–34. The capacitance is monitored at points 35 using leads 36 which are connected to capacitance meter 2.

A preferred flow cell assembly 1 for mounting the simulated or naturally fractured material therein is disclosed in Serial Number 260,350, filed on Oct. 20, 1988. Two of the co-inventors of Serial Number 260,350 are inventors of the present invention. Serial Number 260,350 is hereby incorporated by reference for all that it discloses.

As indicated in FIG. 1, the fluidic system includes fluid supply tanks 3 and 4, an inert gas supply 5 for pressurizing the system, the pressure of which is regulated via regulator 10 and monitored at guage 11, a fluid collection tank 6, fluid flow control valves 13-28 and inline filters 30-31, which may be obtained from Nupro, Inc. (90 micron, Part No. SS-4TF). To maintain and control fluid temperature during testing, the fluid supply lines may be immersed in heated liquid bath 9, which may be a Cole Palmer immersion circulator Model 1266-02 with temperature controller. To prevent excessive heat loss at the flow cell assembly 1, its outer surfaces may be wrapped with a heat tape 38, such as Thermolyne Brisk which may be connected to a suitable temperature controller such as those supplied by Valco, Inc.

To monitor fluid flow rates during testing, separate flow meters 7 and 8 are utilized to monitor the test fluids supplied from tanks 3 and 4. These flow meters may be Micromotion Model D-6's, which have a range of 0 to 1 lb/min. and are known to provide suitable accuracy.

The pressure drop across the flow cell should be accurately monitored through the use of a pressure transducer. A suitable transducer for this application is a Heise Model 621, which has a range of 0 to 10 psi. The output of the pressure transducer may be read via any suitable digital or analog multimeter, such as a Kiethly Model 195A.

Capacitance meter 2 may be a GenRad Model 1658 RLC digibridge or suitable alternative. Leads 36 from capacitance meter 2 are to be connected to the fracture faces in a manner which those skilled in the art would recognize as capable of providing a true reading of capacitance when a voltage differential is applied across the fracture faces. Aluminum posts 35, placed in electrical contact with the conductive fracture faces, have been successfully utilized for this purpose.

To provide a more homogeneous flow and to overcome slugging of the two fluids at the entrance of the fracture, a concentric tube inlet 29 (i.e., a tube within a tube) was constructed. The inner tube may advantageously provide the flow of the oil-like fluid, while the larger, outer the (annulus) can provide the flow of water. It is preferred that the two tubes end about 1/16 inch away from the fracture opening inside the flow cell; thus allowing mixing of both liquid phases before introduction into the fracture.

Prior to, and between tests, cleaning of the fracture faces should be conducted. It has been found that sequential flushing with de-ionized water, isopropyl alcohol and nitrogen is effective in this regard. These materials may be introduced at fitting 34 of the system. During testing, when fluid supplies are nearly depleted, make-up fluids may be added to tanks 3 and 4 via fittings 33 and 34, respectively.

Outputs from the various instruments may be recorded manually or fed into a data acquisition system. A micro computer such as an IBM PC-AT may be advantageously used for this or data reduction purposes.

The following examples are illustrative of the present invention:

EXAMPLE 1

This example demonstrates the utility of the method and system of the present invention when simulated smooth-surface fractures are utilized to study multiphase fluid saturations.

The smooth fracture was made by cutting two aluminum blocks, each 2.0 by 1.02 by 3.1 inch. Steel pins 35 were pressed into holes made in the top side of each aluminum block. These pins were used for the electrical connection in the capacitance measurement. The flow cell assembly 2 disclosed in detail in Serial Number 260,350 was utilized for mounting the aluminum blocks therein. The procedures disclosed within Serial Number 250,350 for properly mounting test sample blocks within the flow cell were utilized and are preferred for employment in the present invention.

Once assembled, the flow cell was laid flat and the inlet and outlet lines attached. The pressure transducer 12 and the outlet line were installed so that they were hydraulically level with the fracture. This assured that no differential pressure was introduced from head pressure.

Supply tank 3 was filled with a brine containing 10% NaCl by weight. Tank 4 was filled with decane for oil-phase simulation. The core cell and test fluids were heated overnight to the same constant temperature (29° C.). This was done since any temperature difference or temperature change between the core cell and the fluids will affect the capacitance readings.

A capacitance versus fluid saturation calibration was performed with the fracture volume at 3 cc. The fracture was first filled with the brine solution and capacitance measured. This was the 100% water saturation value. Thereafter, capacitance data were taken at several different volumes of brine and decane in the fracture. These are presented in Table 1, below:

TABLE 1

| Volume (cc) | | Capacitance | Water Saturation |
|---|---|---|---|
| Water | Decane | ($\mu$F) | (%) |
| 3.0 | 0.0 | 37.3 | 100.0 |
| 2.5 | 0.5 | 31.4 | 83.2 |
| 2.0 | 1.0 | 26.4 | 69.0 |
| 1.5 | 1.5 | 20.3 | 51.7 |
| 1.0 | 2.0 | 13.9 | 33.5 |
| 0.5 | 2.5 | 7.8 | 16.2 |
| 0.0 | 3.0 | 2.1 | 0.0 |

Figure 2:
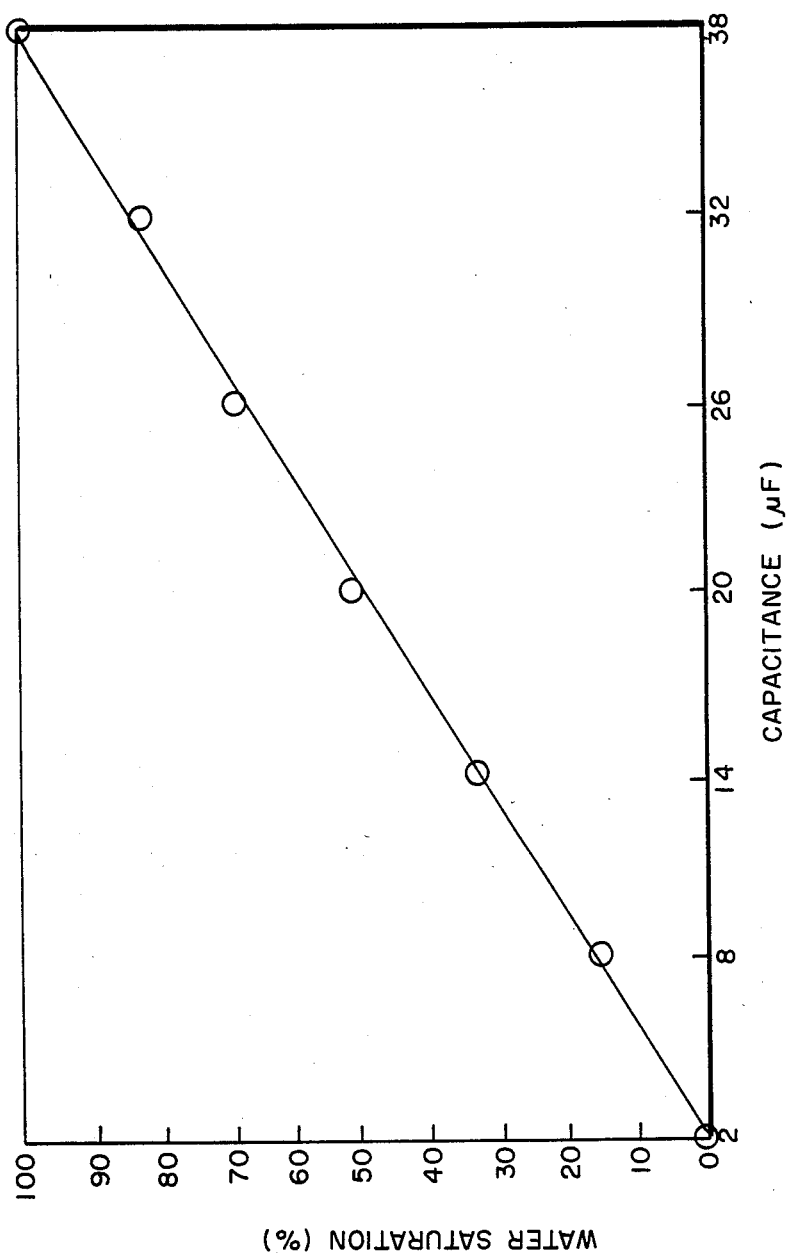
FIG. 2 is a graph presenting the relationship between measured capacitance and water saturation for an experiment conducted in accordance with the present invention.

As may be seen fom the data of Table 1, water saturation, as calculated from Equation 1, supra, is directly proportional to the volume of water (brine) present in the fracture. Since a linear relationship was found to exist, by knowing the 100% water and 100% capacitance values, intermediate saturation values are proportioned therefrom. A plot of the capacitance versus water saturation values of Table 1 is presented in FIG. 2.

The fracture aperture was changed to 0.0136 inches, creating a fracture volume of 0.7 cm$^3$. Next, atmospheric pressure, that is, the pressure on the outlet side of the flow cell 1 was determined. This was done by opening valves 25, 26 and 27 and flowing air into valve 27 to remove entrained water present. Next valves 26 and 27 were closed. The reading obtained by pressure transducer 12 under these conditions was the atmospheric pressure used to obtain the differential pressure across the fracture. Thereafter, valves 25, 26 and 27 were closed, as were valves 15-18.

Fluid supply tanks 3 and 4 were next pressurized with nitrogen supplied by tank 5 and regulated by regulator 10. The dynamic test began by slowly filling the system with the brine solution by opening valves 18, 19, 20 and 25. After initial water wetting, the decane from tank 4 was introduced by opening valves 16, 21, 22 and 24. A total flow rate of 20 cc/min was established; with the flow rates of brine and decane varied at flow control 24 and 25 for test purposes.

Data obtained are presented below in Table 2.

To fabricate the simulated rough fracture, a sandstone core sample was ground up and sieved. Sand with grain sizes between 0.0025 and 0.0059 in. was glued to one set of aluminum blocks, and sand with grains sizes between 0.0059 and 0.0117 in. was glued to another set of aluminum cores.

Tests were conducted using the procedures described in Example 1, with the exception that, in this example, decane was employed as the initial "wetting" fluid. Data obtained using the small grain size simulated fracture are presented in Table 3 and data obtained using the large grain size simulated fracture are presented in Table 4. As may be seen, the presence of the sand grains do not inhibit the overall conductivity of the aluminum fracture blocks.

TABLE 2

DATA FOR SMOOTH ALUMINUM VERTICAL FRACTURE FLOW RATE OF 20 CC/MIN

| Inlet Fluid Rates (cc/min) | | Differential Pressure (psi) | Capacitance Reading ($\mu$F) | Calculated Fracture Water Saturation (%) | Calculated Water Relative Permeability | Calculated Decane Relative Permeability |
|---|---|---|---|---|---|---|
| H$_2$O | Decane | | | | | |
| 20 | 0 | 0.112 | 85.6 | 100.0 | 1.000 | 0.000 |
| 16 | 4 | 0.112 | 69.0 | 77.7 | 0.800 | 0.164 |
| 12 | 8 | 0.111 | 59.5 | 65.0 | 0.605 | 0.331 |
| 8 | 12 | 0.103 | 49.5 | 51.6 | 0.435 | 0.534 |
| 4 | 16 | 0.099 | 35.6 | 33.0 | 0.226 | 0.741 |
| 0 | 20 | 0.092 | 17.0 | 8.0 | 0.000 | 0.997 |

Aperture set to 0.0136 inches.
Viscosity of brine = 1.05 cp
Viscosity of decane = 0.86 cp
$C_{decane}$ at 100% = 11 $\mu$F

EXAMPLE 2

This example demonstrates the utility of the method and system of the present invention when simulated rough fractures are employed.

TABLE 3

ARTIFICIAL ROUGH FRACTURE DATA FOR INITIALLY DECANE-WET SMALL GRAIN SIZE FRACTURES

| Inlet Fluid Rates (cc/min) | | Differential Pressure (psi) | Capacitance Reading ($\mu$F) | Calculated Fracture Water Saturation (%) | Calculated Water Relative Permeability | Calculated Decane Relative Permeability |
|---|---|---|---|---|---|---|
| H$_2$O | Decane | | | | | |
| 0.0 | 50.0 | 0.405 | 0.3 | 0.0 | 0.000 | 1.000 |
| 10.0 | 39.7 | 0.585 | 6.3 | 12.0 | 0.169 | 0.550 |
| 19.9 | 30.1 | 0.697 | 8.0 | 15.3 | 0.282 | 0.360 |
| 29.9 | 19.9 | 0.690 | 11.7 | 22.7 | 0.428 | 0.234 |
| 39.8 | 10.0 | 0.720 | 14.3 | 27.8 | 0.547 | 0.112 |
| 45.0 | 5.0 | 0.761 | 15.0 | 29.3 | 0.585 | 0.053 |
| 39.8 | 10.1 | 0.736 | 15.4 | 30.0 | 0.535 | 0.111 |
| 30.0 | 20.0 | 0.744 | 14.1 | 27.5 | 0.399 | 0.218 |
| 20.0 | 30.1 | 0.744 | 11.1 | 21.5 | 0.266 | 0.328 |
| 9.9 | 39.9 | 0.680 | 8.6 | 16.5 | 0.144 | 0.475 |
| 0.0 | 50.1 | 0.590 | 5.8 | 11.0 | 0.000 | 0.688 |
| 9.9 | 39.9 | 0.655 | 10.2 | 19.7 | 0.149 | 0.493 |
| 19.9 | 29.8 | 0.750 | 12.0 | 23.3 | 0.262 | 0.322 |
| 29.8 | 19.7 | 0.711 | 13.8 | 26.9 | 0.414 | 0.224 |
| 40.1 | 9.9 | 0.741 | 15.8 | 30.9 | 0.535 | 0.108 |
| 45.2 | 5.3 | 0.750 | 16.5 | 32.3 | 0.596 | 0.057 |

Viscosity of water = 1.05 cp
Viscosity of decane = 0.86 cp
$C_{C10}$ (100%) = 0.3 $\mu$F

TABLE 4

ARTIFICIAL ROUGH FRACTURE DATA FOR INITIALLY DECANE-WET LARGE GRAIN FRACTURE

| Inlet Fluid Rates (cc/min) | | Differential Pressure (psi) | Capacitance Reading ($\mu$F) | Calculated Fracture Water Saturation (%) | Calculated Water Relative Permeability | Calculated Decane Relative Permeability |
|---|---|---|---|---|---|---|
| H$_2$O | Decane | | | | | |
| 0.0 | 52.2 | 1.072 | 6.3 | 0.0 | 0.000 | 1.000 |
| 9.9 | 40.1 | 1.349 | 36.8 | 18.6 | 0.191 | 0.635 |
| 20.0 | 30.1 | 1.215 | 50.5 | 27.0 | 0.429 | 0.529 |
| 29.8 | 19.8 | 1.394 | 65.0 | 35.9 | 0.557 | 0.303 |
| 39.9 | 10.2 | 1.485 | 72.8 | 40.6 | 0.701 | 0.147 |
| 48.9 | 4.9 | 1.674 | 84.0 | 47.5 | 0.762 | 0.063 |

TABLE 4-continued
ARTIFICIAL ROUGH FRACTURE DATA FOR INITIALLY DECANE-WET LARGE GRAIN FRACTURE

| Inlet Fluid Rates (cc/min) | | Differential Pressure | Capacitance Reading | Calculated Fracture Water Saturation | Calculated Water Relative | Calculated Decane Relative |
|---|---|---|---|---|---|---|
| H₂O | Decane | (psi) | (μF) | (%) | Permeability | Permeability |
| 40.0 | 10.1 | 1.695 | 80.5 | 45.3 | 0.615 | 0.127 |
| 30.1 | 20.2 | 1.646 | 73.0 | 40.8 | 0.477 | 0.262 |
| 19.9 | 30.0 | 1.770 | 60.0 | 32.8 | 0.293 | 0.362 |
| 9.9 | 39.6 | 1.773 | 50.5 | 27.0 | 0.146 | 0.477 |
| 0.0 | 49.8 | 1.374 | 34.1 | 17.0 | 0.000 | 0.774 |
| 0.0 | 49.7 | 1.368 | 36.9 | 18.7 | 0.000 | 0.775 |
| 10.0 | 39.9 | 1.810 | 50.1 | 26.8 | 0.144 | 0.471 |
| 19.9 | 30.5 | 1.837 | 61.5 | 33.7 | 0.282 | 0.355 |
| 30.0 | 19.6 | 1.487 | 74.5 | 41.7 | 0.526 | 0.281 |
| 39.7 | 9.7 | 1.575 | 84.3 | 47.7 | 0.657 | 0.132 |
| 45.0 | 4.9 | 1.680 | 91.0 | 51.7 | 0.698 | 0.062 |
| 39.8 | 10.1 | 1.621 | 83.5 | 47.2 | 0.640 | 0.133 |
| 30.1 | 19.8 | 1.673 | 78.5 | 44.1 | 0.469 | 0.253 |
| 19.8 | 29.6 | 1.806 | 62.8 | 34.5 | 0.286 | 0.350 |
| 10.0 | 39.6 | 1.839 | 53.5 | 28.8 | 0.142 | 0.460 |
| 0.0 | 49.7 | 1.426 | 37.9 | 19.3 | 0.000 | 0.744 |

Viscosity of water = 1.05 cp
Viscosity of decane = 0.86 cp
$CC_{10}(100\%) = 6.3\ \mu F$

EXAMPLE 3

Two carbonate cores, each having low matrix permeability (k=1.6 md), were used in these tests. These naturally-fractured cores were cut into blocks approximately 1"x1"x3", with the fracture running longitudinally through the center. For use in the flow cell assembly of Serial Number 260,350, these core blocks were bonded to aluminum blocks for mounting therein in the manner disclosed in that application.

As mentioned, for capacitance measurements to be taken on naturally-fractured cores epoxied onto aluminum blocks, the parallel fracture faces as well as the top side of each epoxied core/block had to be finely coated with a conductive material (gold, in this case). A commercial sputter coater was used for this operation, which was conducted in the usual, well-known manner. Also, thin strips of a conductive metal (aluminum) were laid over the top of the rock/block assembly connecting the two pieces to ensure a continuous conductive surface in the case of the epoxy bond breaking. Total isolation of the rock/block fracture from the cell holder was important to prevent erroneous capacitance readings.

Tests were conducted in the manner described in Example 1. The two fluids used were a 5% sodium chloride brine (water) and decane (oil). Flow tests were run with a fracture aperture set to 0.025 inch and a nominal overall flow rate of 10 cc/min. Results are presented in Table 5, below.

TABLE 5
DATA FOR NATURAL FRACTURE NOMINAL FLOW RATE OF 10 CC/MIN

| Inlet Fluid Flow Rates (cc/min) | | Differential Pressure | Capacitance Reading | Calculated Fracture Water Saturation | Calculated % Water | Calculated Oil Relative |
|---|---|---|---|---|---|---|
| Water | Decane | (psi) | (μF) | (%) | Saturation | Permeability |
| 9.40 | 0.00 | .024 | 449 | 100.0 | 1.000 | 0.000 |
| 0.00 | 10.10 | .036 | 61 | 13.6 | 0.000 | 0.592 |
| 9.45 | 0.00 | .050 | 278 | 61.9 | 0.489 | 0.000 |
| 7.89 | 2.14 | .080 | 265 | 59.0 | 0.252 | 0.056 |
| 6.16 | 4.20 | .080 | 230 | 51.2 | 0.197 | 0.110 |
| 4.00 | 6.15 | .077 | 208 | 46.3 | 0.133 | 0.167 |
| 1.91 | 8.07 | .060 | 156 | 34.8 | 0.081 | 0.281 |
| 0.00 | 9.94 | .042 | 111 | 24.7 | 0.000 | 0.495 |
| 1.82 | 8.10 | .046 | 141 | 31.4 | 0.101 | 0.368 |
| 4.12 | 5.96 | .074 | 200 | 44.6 | 0.142 | 0.168 |
| 5.84 | 3.95 | .080 | 230 | 51.2 | 0.187 | 0.103 |
| 7.98 | 2.02 | .090 | 250 | 55.7 | 0.226 | 0.047 |
| 9.84 | 0.00 | .064 | 343 | 76.4 | 0.393 | 0.000 |

Density of water = 63.8 lb/ft³
Density of decane = 45.3 lb/ft³
Viscosity of water = 1.04 cp
Viscosity of decane = 0.86 cp The invention and its broader aspects is not limited to the specific details shown and described. Although the invention has been described with preferred embodiments, it is to be understood that modifications and variations may be made without departing from the spirit and scope of the invention as those skilled in the art will readily understand.

What is claimed is:

1. A method for determining fluid saturation within a fracture of a fractured material, having at least a first and second fracture face, comprising the steps of:
   (a) establishing a functional relationship between fluid saturation and capacitance for a multiple component fluid;

(b) introducing the fluid between the fracture faces;
(c) measuring electrical capacitance between the fracture faces; and
(d) determining fluid saturation from the capacitance measurement of step (b) and the relationship established in step (a).

2. The method of claim 1, wherein the fluid of step (a) is a multi-phase fluid having at least a first phase and a second phase.

3. The method of claim 2, wherein the relationship of step (a) is established by measuring capacitance at 100% saturation for each phase of the milti-phase fluid.

4. The method of claim 3, wherein a continuous flow of the multi-phase fluid is established between the fracture faces of the fractured material.

5. The method of claim 4, wherein a first phase of the multi-phase fluid is an aqueous brine and a second phase of the multi-phase fluid is a hydrocarbonaceous fluid.

6. The method of claim 5, wherein the second phase of the multi-phase fluid is decane.

7. The method of claim 6, wherein the fractured material comprises a conductive metal having grains of sand affixed thereto to simulate reservoir fracture faces.

8. The method of claim 6, wherein the fractured material is naturally fractured reservoir media.

9. The method of claim 8, wherein the fracture faces of the naturally-fractured reservoir media are sputter coated with a conductive material.

10. The method of claim 9, wherein the conductive material is gold.

11. The method of claim 4, further comprising:
(e) changing the rate of flow of fluid between the fracture faces of the fractured material and repeating steps (c)-(d).

12. The method of claim 11, further comprising:
(f) repeating step (e) a plurality of times.

13. The method of claim 12, further comprising the step of reading and storing measured data through the use of a computerized data acquisition system.

14. A system for determining fluid saturation within a fracture of a fractured material having at least a first and second fracture face, comprising:
(a) a flow cell for mounting the fractured material therein;
(b) means for measuring the capacitance between the fracture faces; and
(c) means for providing a regulated flow of test fluid.

15. The system of claim 14, wherein said means for providing a regulated flow of test fluid is pressurized non-recirculatory fluid system.

16. The system of claim 15, wherein pressurization is provided by an inert gas.

17. The system of claim 14, wherein said means for providing a regulated flow of test fluid comprises at least two independently controlled fluid delivery systems capable of providing a multi-phase fluid to the fracture faces within the flow cell.

18. The system of claim 17, further comprising means for measuring fluid flow between the fracture faces so that simulated reservoir flow conditions may be set and maintained.

19. The system of claim 18, further comprising means for measuring the pressure drop across the fracture aperture resulting from the flow of fluid through the aperture so that simulated reservoir flow conditions may be set and maintained.

20. The system of claim 19, further comprising means for regulating fluid supply temperature.

21. The system of claim 20, further comprising means for regulating flow cell temperature.

* * * * *